United States Patent [19]
Yamamoto et al.

[11] Patent Number: 5,283,193
[45] Date of Patent: Feb. 1, 1994

[54] PROCESS FOR PRODUCING OPTICALLY ACTIVE α-SUBSTITUTED ORGANIC ACID AND MICROORGANISM AND ENZYME USED THEREFOR

[75] Inventors: Keizou Yamamoto; Kazumasa Otsubo; Kazuhiko Oishi, all of Miyazaki, Japan

[73] Assignee: Asahi Kasei Kogyo K.K., Osaka, Japan

[21] Appl. No.: 799,879

[22] Filed: Nov. 27, 1991

Related U.S. Application Data

[63] Continuation of Ser. No. 370,964, Jun. 26, 1989, abandoned.

[30] Foreign Application Priority Data

Jun. 27, 1988 [JP] Japan .................. 63-156911

[51] Int. Cl.$^5$ ............................ C12P 7/40
[52] U.S. Cl. .................................. 435/280
[58] Field of Search ........................ 435/280

[56] References Cited

U.S. PATENT DOCUMENTS

| | | | |
|---|---|---|---|
| 4,080,259 | 3/1978 | Boesten et al. | 435/280 |
| 4,443,548 | 4/1984 | Oshima et al. | 435/280 |
| 4,812,403 | 3/1989 | Boesten et al. | 435/280 |

FOREIGN PATENT DOCUMENTS

| | | |
|---|---|---|
| 54-14668 | 6/1979 | Japan . |
| 61-56086 | 3/1986 | Japan . |
| 61-88894 | 5/1986 | Japan . |
| 62-282089 | 12/1986 | Japan . |
| 62-55098 | 3/1987 | Japan . |
| 8607386 | 12/1986 | PCT Int'l Appl. . |

OTHER PUBLICATIONS

Fukuda, Y. et al, *J. Ferment. Technol.*, 51:393-397 (1973).

*Primary Examiner*—Lester L. Lee
*Attorney, Agent, or Firm*—Sughrue, Mion, Zinn, Macpeak & Seas

[57] ABSTRACT

A process for producing an optically active α-substituted organic acid represented by formula (II), comprising the steps of (a) treating a racemic substituted nitrile or amide represented by formula (I) with a microorganism selected from the group consisting of the microorganisms of genuses Alcaligenes, Pseudomonas, Rhodopseudomonas, Corynebacterium, Acinetobacter, Bacillus, Mycobacterium, Rhodococcus and Candida, or preparations thereof; and (b) recovering the resulting optically active α-substituted organic acid represented by formula (II):

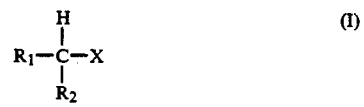

(I)

wherein $R_1$ and $R_2$ each represent a halogen atom, a hydroxyl group, a substituted or unsubstituted alkyl group, a substituted or unsubstituted cycloalkyl group, a substituted or unsubstituted alkoxy group, a substituted or unsubstituted aryl group, a substituted or unsubstituted aryloxy group or a substituted or unsubstituted heterocyclic group with the proviso that $R_1$ and $R_2$ are different from each other; and X represents a nitrile group or an amido group,

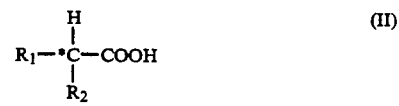
(II)

wherein $R_1$ and $R_2$ are as defined above.

2 Claims, 1 Drawing Sheet

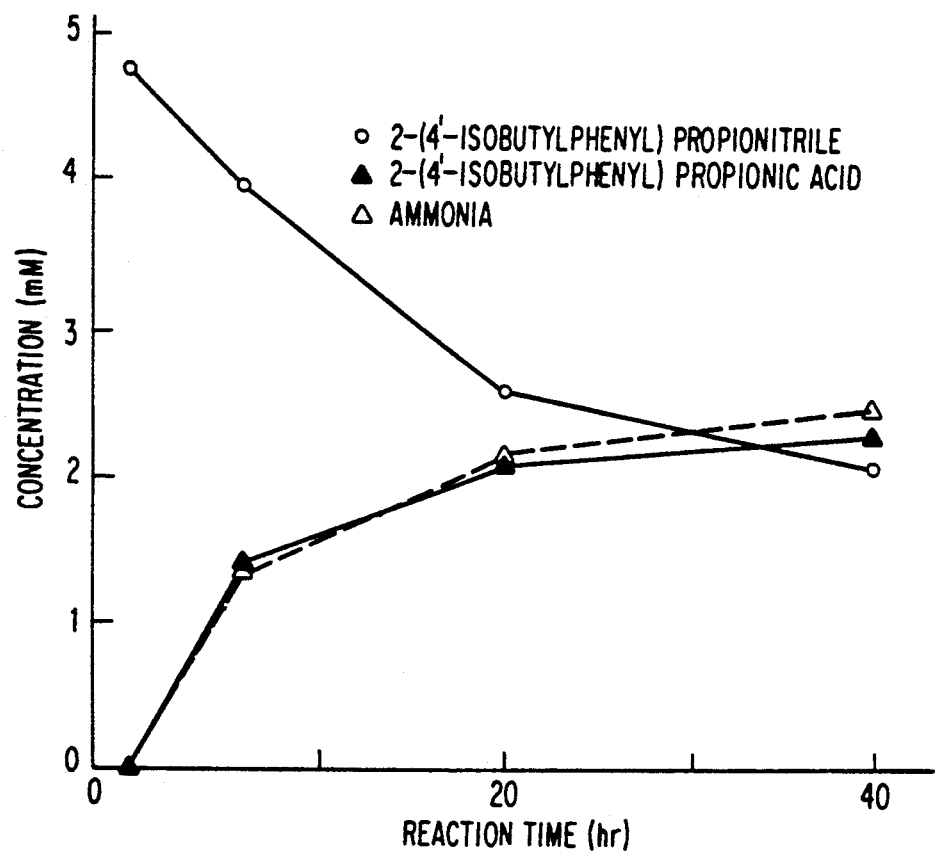

PROCESS FOR PRODUCING OPTICALLY ACTIVE α-SUBSTITUTED ORGANIC ACID AND MICROORGANISM AND ENZYME USED THEREFOR

This is a continuation of application Ser. No. 07/370,964 filed Jun. 26, 1989, now abandoned.

FIELD OF THE INVENTION

This invention relates to a process for producing an optically active α-substituted organic acid and microorganism and enzyme used therefor.

Optically active α-substituted organic acids obtained by the process of the present invention are such as antipyretic, analgesic or antiphlogistic agents; as raw materials thereof, such as antibiotics and β-blockers; as agricultural chemicals, such as herbicides and insecticides or raw materials thereof; as raw materials for compounds having super dielectric properties and as optical resolving reagents.

BACKGROUND OF THE INVENTION

Known processes for producing optically active α-substituted organic acids from racemic α-substituted nitriles or u-substituted amides by the biochemical action of microorganisms or preparations thereof include those processes disclosed in, for example, PCT Patent Application No. 500004/1988 (WO 8607386) and JP-A-60-188355 (U.S. Pat. No. 4,812,403) (the term "JP-A" as used herein means an "unexamined published Japanese patent application"). These publications also disclose that the microorganisms used for said processes can be used for the production of optically active amino acids from aminonitriles or amino acid amides.

However, there are scarcely any known processes for producing optically active α-substituted organic acids other than amino acids from the corresponding racemic nitriles or amides by biochemical action. There are known only processes for producing optically active α-oxy acids from α-oxy acid amide compounds and specific hydroxynitriles. There are only three known microorganisms used for these processes. That is, a bacterium belonging to genus Aeromonas, a bacterium belonging to genus Moraxella and a yeast belonging to genus Torulopsis (see, JP-A-61-88894 and JP-B-54-14668 (the term "JP-B" as used herein means an "examined Japanese patent publication")).

SUMMARY OF THE INVENTION

It is an object of the present invention to provide a process for producing optically active α-substituted organic acids useful as raw materials in medical, agricultural and industrial fields from the corresponding racemic u-substituted nitriles or α-substituted amides by the action of microorganisms or preparations thereof.

It is another object of the present invention to provide microorganisms used for the above-described process.

The present inventors have discovered microorganisms capable of exclusively forming said optically active α-substituted organic acids to achieve the abovedescribed objects. As a result, the present inventors have found microorganisms which have the ability to convert racemic α-substituted nitriles or amides represented by formula (I) into optically active α-substituted organic acids represented by formula (II). Further, it has been found that the optically active α-substituted organic acids formed by the action of the microorganisms are scarcely racemized, decomposed or utilized. The present invention has been achieved on the basis of these findings.

Accordingly, the present invention provides a process for producing an optically active organic acid represented by formula (II), which comprises (a) treating a racemic o-substituted nitrile or amide represented by formula (I) with a microorganism selected from the group consisting of the microorganisms of genera Alcaligenes, Pseudomonos, Rhodopseudomonas, Corynebacterium, Acinetobacter, Bacillus, Mycobacterium, Rhodococcus and Candida, or preparations thereof; and (b) recovering the formed optically active α-substituted organic acid represented by formula (II):

and

In formula (I), X represents a nitrile group or an amido group. In formulas (I) and (II), $R_1$ and $R_2$ each represent a halogen atom, a hydroxyl group, an alkyl group, a cycloalkyl group, an alkoxy group, an aryl group, an aryloxy group or a heterocyclic group with the proviso that the groups $R_1$ and R2 are always different from each other.

BRIEF DESCRIPTION OF THE DRAWING

The FIGURE is a graph showing the progress of the production of 2-(4'-isobutylphenyl)propionic acid by using purified nitrilase, wherein the ordinate axis represents concentration and the abscissa axis represents reaction time.

DETAILED DESCRIPTION OF THE INVENTION

The present invention is discussed in more detail below.

Examples of halogen represented by $R_1$ and $R_2$ in formulae (I) and (II) include fluorine, chlorine, iodine and bromine. As the alkyl group and the alkoxy group, those having from 1 to 8 carbon atoms are preferred and those having from 1 to 3 carbon atoms are particularly preferred. Preferred examples of the cycloalkyl group are those having from 3 to 8 carbon atoms and those having from 3 to 6 carbon atoms are more preferred. Examples of the aryl group include phenyl and naphthyl. Examples of the aryloxy group include phenyloxy and naphthyloxy. Preferred examples of the heterocyclic group are those having one or more hetero-atoms selected from among nitrogen, oxygen and sulfur and having from 3 to 15 carbon atoms, more preferably those having 1 to 4 of heteroatoms. Examples of the heterocyclic groups include thiophene, indole,

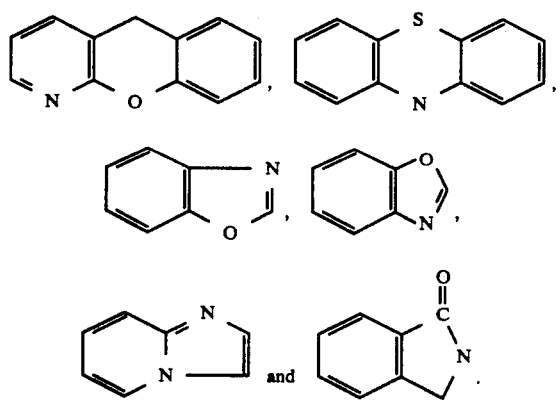

Hydrogen atoms attached to the carbon atoms of the alkyl group, alkoxy group, cycloalkyl group, aryl group and aryloxy group and hydrogen atoms attached to the carbon atoms and the nitrogen atom of the heterocyclic group may be optionally substituted by one or more substituent groups. Examples of suitable substituent groups include a halogen atom such as fluorine, chlorine, iodine and bromine, a hydroxyl group, a thiol group, a nitro group, an amino group, an aryl group (e.g., phenyl or naphthyl group), an aryloxy group (e.g., phenyloxy or naphthyloxy group), a heterocyclic group containing one or more hetero-atoms such as a nitrogen atom, an oxygen atom and a sulfur atom and having from 3 to 15 carbon atoms, an alkyl group having from 1 to 8 carbon atoms, an alkoxy group having from 1 to 8 carbon atoms and an acyl group having from 1 to 10 carbon atoms. Hydrogen atoms attached to the carbon atoms of the above-described substituent groups and hydrogen atoms attached to the carbon atoms and the nitrogen atom of the above heterocyclic group may be further substituted by one or more of the above-described substituent groups.

When either one of $R_1$ and $R_2$ is a highly sterically hindered group such as a halogen atom, an aryl group, an aryloxy group or a residue of a heterocyclic ring, or when either one of $R_1$ and $R_2$ is a group substituted by the highly sterically hindered group, products having very high optical purity can be obtained.

Typical compounds of formula (II), obtained by the process of the present invention, are illustrated in the following Table 1.

TABLE 1

| $R_1 \overset{H}{\underset{R_2}{-\overset{|}{\underset{|}{*C}}-COOH}}$ | General name of compound |
|---|---|
| CH₃-CHCH₂-⟨phenyl⟩-*C(H)(CH₃)-COOH | Ibuprofen |
| CH₃O-⟨naphthyl⟩-*C(H)(CH₃)-COOH | Naproxen |
| ⟨pyrano⟩-*C(H)(CH₃)-COOH | Pranoprofen |
| F-⟨biphenyl⟩-*C(H)(CH₃)-COOH | Flurbiprofen |
| Ph-C(=O)-⟨phenyl⟩-*C(H)(CH₃)-COOH | Ketoprofen |
| Ph-O-⟨phenyl⟩-*C(H)(CH₃)-COOH | Fenoprofen |

TABLE 1-continued
$$R_1 - \overset{H}{\underset{R_2}{\overset{|}{*C}}} - COOH$$
| Structure | General name of compound |
|---|---|
| 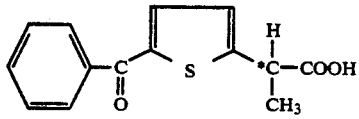 | Tiaprofenic acid |
| 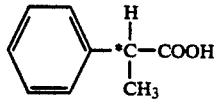 | α-Phenylpropionic acid |
| 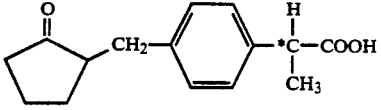 | Loxoprofen |
| 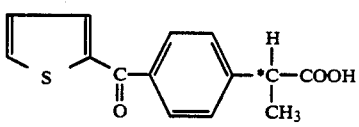 | Suprofen |
| 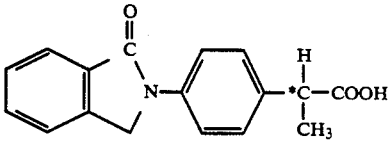 | Indoprofen |
| 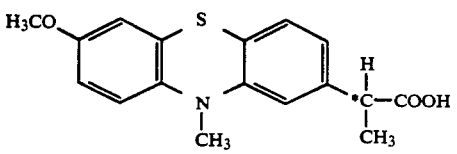 | Protizinic acid |
| 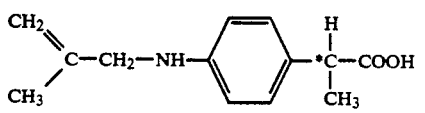 | Alminoprofen |
| 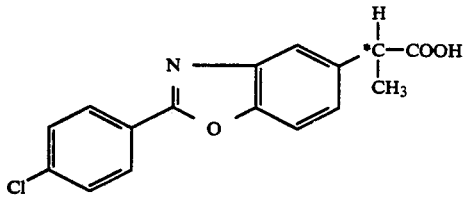 | Benoxaprofen |
| 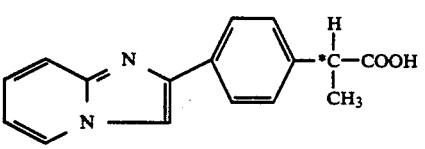 | Miroprofen |
| 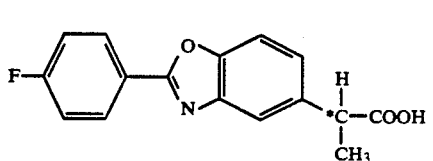 | Flunoxaprofen |

TABLE 1-continued

| R₁—*C(H)(R₂)—COOH | General name of compound |
|---|---|
| 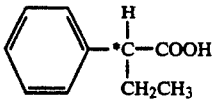 | 2-Phenylbutyric acid |
| 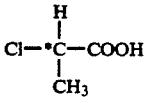 | 2-Chloropropionic acid |
| 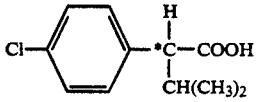 | 4-Chloro-α-(1-methylethyl)phenyl acetic acid |
| 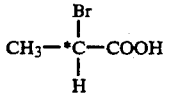 | 2-Bromopropionic acid |
| 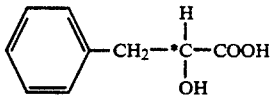 | β-Phenyl lactic acid |
| 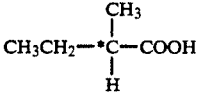 | 2-Methylbutyric acid |
| 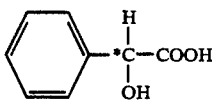 | Mandelic acid |
| 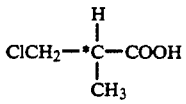 | 3-Chloro-2-methylpropionic acid |
| 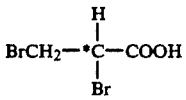 | 2,3-Dibromopropionic acid |
| 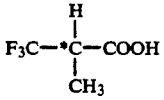 | 3-Trifluoro-2-methylpropionic acid |
| 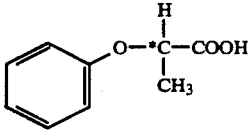 | 2-Phenoxypropionic acid |
| 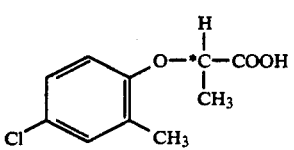 | 2-(2-Methyl-4-chlorophenoxy)-propionic acid |

TABLE 1-continued $$R_1 - \overset{H}{\underset{R_2}{\overset{|}{C}}} - COOH$$

General name of compound

| Structure | General name of compound |
|---|---|
| 2,4-dichlorophenyl-O-*C(H)(CH₃)-COOH | 2-(2,4-Dichlorophenoxy)propionic acid |

The compounds represented by formula (I) which are used as the starting materials in the present invention can be prepared by conventional methods as described, for example, in JP-A-51-70744, JP-A-51-122036, U.S. Pat. No. 4,186,270 and Synthesis, 8, 645 (1986).

The microorganisms which can be used in the present invention are those selected from the group consisting of the microorganisms of genuses Alcaliqenes, Pseudomonas, Rhodopseudomonas, Corynebacterium, Acinetobacter, Bacillus, Mycobacterium, Rhodococcus and Candida.

Specifically, the following microorganisms can be used.
Alcaligenes faecalis ATCC 8750,
Pseudomonas fluorescens NRRL B-981 (IFO 3925) (the term IFO as used herein means the microorganism on deposit at the Institute for Fermentation, Osaka, Japan),
Pseudomonas fluorescens IFO 3081,
Rhodopseudomonas sphaeroides ATCC 11167,
Corynebacterium nitrilophilus ATCC 21419,
Corynebacterium sp. KO-2-4 (FERM BP-2353),
Acinetobacter sp. AK 226 (FERM BP-2451),
Bacillus subtilis CN5 (FERM BP-2354),
Mycobacterium sp AC777 (FERM BP-2352),
Rhodococcus sp. AK 32 (FERM BP-1046),
Pseudomonas vesicularis ATCC 11426, and
Candida tropicalis ATCC 20311.

A live culture of the microorganism Rhodococcus sp. AK 32 is on deposit at the Fermentation Research Institute, Japan, under the above designated number. The mycological properties thereof are described in European Patent 204,555 (1986).

Corynebacterium sp. KO-2-4, Bacillus subtilis CN5 and Mycobacterium sp. AC777 were newly isolated as nitrile-utilizing bacteria from soil and are on deposit at the Fermentation Research Institute, Japan, under the above designated numbers.

Acinetobacter sp. AK 226 has been already isolated to form unsaturated organic acids such as acrylic acid or methacrylic acid from the corresponding nitrile compounds (see, JP-B-63-2596 (the term "JP-B" as used herein means an "examined Japanese patent publication")). This strain is on deposit at the Fermentation Research Institute, Japan.

The mycological properties of Corynebacterium sp. KO-2-4, Bacillus subtilis CN5, Mycobacterium sp. AC777 and Acinetobacter sp. AK 226 are as follows:

| Item | Strain | | | |
|---|---|---|---|---|
| | KO-2-4 | CN5 | AC777 | AK226 |
| (a) morphological characteristics | | | | |
| 1. shape and size of cell | rod | rod | rod | rod |
| | 0.6–0.9 × 1.5–2.4 μm | 0.6–1.0 × 1.4–2.2 μm | 0.4–0.7 × 1.5–2.5 μm | 1.0–1.2 × 1.4–2.7 μm |
| 2. polymorphism of cell | Elongated cells and snapping division are observed | none | none | none |
| 3. motility | none | flagellate mobile | none | none |
| 4. sporulation | no | formed | no | no |
| 5. Gram staining | + | mainly + | + | − |
| 6. acid-fast staining | − | − | mainly + | − |
| (b) Growth state in various culture mediums | | | | |
| 1. Bouillon agar plate culture | orbicular, glossy, light yellowish white. | orbicular, glossy, light yellowish white, translucent. | orbicular, smooth, non-glossy, light yellowish white. | orbicular, translucent, glossy, light yellowish white. |
| 2. Bouillon agar slant culture | moderate growth, glossy surface, light yellowish white. | good growth, glossy, light yellowish white, translucent. | moderate growth, non-glossy, light yellowish white. | moderate growth, smooth surface, glossy, translucent, light yellowish white. |
| 3. Bouillon liquid culture | moderate growth with no formation of a pellicle, no formation of a precipitate with growth. | good growth with no formation of a pellicle, no formation of a precipitate with growth. | good growth with no formation of a pellicle, no formation of a precipitate with growth. | moderate growth with the formation of a pellicle, and the formation of a precipitate with growth. |
| 4. Bouillon gelatin stab culture | good growth on the surface, no liquefaction of gelatin. | good growth on the surface, liquefaction of gelatin. | good growth on the surface, no liquefaction of gelatin. | good growth on the surface, no liquefaction of gelatin. |
| 5. litmus milk | no change | changed to | no change | no change |

-continued

| Item | Strain | | | |
|---|---|---|---|---|
| | KO-2-4 | CN5 | AC777 | AK226 |
| | | translucent | | |
| (c) physiological characteristics | | | | |
| 1. reduction of nitrate | − | + | − | − |
| 2. denitrification reaction | − | − | − | − |
| 3. MR test | − | − | + | − |
| 4. VP test | − | + | − | − |
| 5. formation of indole | − | − | − | − |
| 6. formation of hydrogen sulfide | − | − | − | − |
| 7. hydrolysis of starch | + | + | − | − |
| 8. citric acid use | − | + | + | + |
| | Koser's culture medium | Koser's culture medium | Koser's culture medium | Simmon's culture medium |
| 9. utilization of inorganic nitrogen source | | | | |
| nitrate | − | − | − | − |
| ammonium salt | − | − | − | − |
| 10. formation of pigment | | | | |
| King A medium | − | − | − | − |
| King B medium | − | − | + | − |
| 11. urease | − | − | + | − |
| 12. oxidase | − | + | − | − |
| 13. catalase | + | + | + | + |
| 14. range for growth | pH 5–10, temperature 15–40° C. | pH 5–10, temperature 15–50° C. | pH 5–10, temperature 5–37° C. | pH 5–12, temperature 10–40° C. |
| 16. behavior against oxygen | facultative anaerobic | aerobic | aerobic | aerobic |
| 17. OF test | − | oxidative | oxidative | − |
| 18. formation of acids and gases from sugar | formation of acid / formation of gas | formation of acid / formation of gas | formation of acid / formation of gas | formation of acid / formation of gas |
| L-arabinose | − / − | − / − | − / − | − / − |
| D-xylose | − / − | − / − | − / − | − / − |
| D-glucose | − / − | − / − | + / − | − / − |
| D-mannose | − / − | − / − | − / − | − / − |
| D-fructose | − / − | − / − | + / − | − / − |
| maltose | − / − | − / − | − / − | − / − |
| sucrose | − / − | − / − | − / − | − / − |
| lactose | − / − | − / − | − / − | − / − |
| trehalose | − / − | − / − | − / − | − / − |
| D-sorbitol | − / − | − / − | − / − | − / − |
| D-mannitol | − / − | − / − | − / − | − / − |
| inositol | − / − | − / − | − / − | − / − |
| glycerol | − / − | − / − | − / − | − / − |
| starch | − / − | − / − | − / − | − / − |
| ethanol | + / − | − / − | − / − | − / − |
| methanol | − / − | − / − | − / − | − / − |
| cellulose | − / − | − / − | − / − | − / − |

On the basis of the above mycological properties, the taxonomic positions of these bacteria were determined according to Bergy's Manual of Determinative Bacteriogy, the 8th edition (1974) and the Manual of Clinical Microbiology, the 4th edition (1985).

The KO-2-4 strain is a bacillus which does not form spores, is aerobic, Gram-positive and catalase positive, is non-flagellate and does not have motility. It is clear that it is a strain belonging to the group of Coryneform bacteria, because it has such polymorphism that in the early stage of growth, it is rod and grown with snapping and then undergoes plastmotomy into rod form. Further, the strain is incapable of decomposing cellulose, is not acid fast, is not an absolute aerobe and is negative in OF test. Thus, it can be identified that the KO-2-4 strain is a bacterium belonging to the genus Corynebacterium.

The CN5 strain is mainly a Gram-positive bacillus and forms spores. Further, it is flagellate and mobile. Thus, it is clear that the strain belongs to the family Bacillaceae. The CN5 strain is aerobic and catalase-positive. Hence, the strain belongs to genus Bacillus. Further, the strain does not form gas from glucose, is capable of hydrolyzing starch, is positive in VP test, is capable of reducing nitrate, is grown at 50° C. and in Bouillon broth containing 7% Nacl and allows citric acid on Koser's citrate medium to be utilized. Accordingly, it can be identified that the strain is *Bacillus subtilis*.

The AC777 strain is an aerobic Gram-positive bacillus, undergoes plastomotomy into rod form and does not form spores. Hence, it belongs to the group of coryneform bacteria. Further, the strain exhibits oxidative in OF test, can form an acid from glucose and is oxidase-negative. Accordingly, it can be identified that the strain belongs to the genus Mycobacterium.

The reaction of the present invention is carried out by bringing a racemic nitrile or amide of formula (I) into contact with the microorganism or a preparation thereof. The term "microorganism or preparation thereof" as used herein refers to cultured medium obtained by culturing the microorganism; cells collected therefrom or treated cells (for example, disintegrated cells or enzyme extracted from the cells); or cells or treated cells immobilized on a carrier by an appropriate method.

The microorganisms of the present invention can be cultured according to conventional methods. Culture mediums known as nutrient sources can be used. Carbon sources including glucose, glycerol, ethanol, sucrose, dextrin and acid; nitrogen sources including ammonium sulfate, ammonium chloride and ammonia; organic nutrient sources including yeast extract, malt extract, peptone and meat extract; and inorganic nutrient sources including phosphoric acid, magnesium, potassium, iron and manganese, can be used in an appropriate combination. If desired, cyano compounds such as isobutyronitrile may be added to accelerate the reaction activity of the microorganisms of the present invention. The pH of the medium is in the general range of from 5 to 10. The culture temperature is 18 to 50° C., preferably 25 to 40° C. The culture is allowed to proceed until activity reaches maximum, generally for 1 to 10 days.

The reaction conditions of the present invention are such that an aqueous solution such as water, a buffer solution or a culture medium or a two phase system consisting of an organic solvent and an aqueous solution can be used as the reaction solution. The racemic compound represented by formula (I) in the form of a powder or a liquid as such is added to the reaction solution. Alternatively, the racemic compound is dissolved in an appropriate solvent and added. The amount of the racemic compound to be added is in the range of 0.01 to 70% by weight, preferably 0.1 to 40% by weight and it is not necessary to completely dissolve the racemic compound in the reaction solution. The concentration of the bacterium to be used for reaction is in the general range of from 0.05 to 20% by weight. The reaction temperature is in the general range of 5 to 80° C., preferably 15 to 60° C., and pH is in the general range of 4 to 11, preferably 6 to 10. The reaction time is generally 1 to 100 hours. The racemic compound represented by formula (I) may be continuously or intermittently added to the reaction solution to replenish the racemic compound so that the concentration of the racemic compound can be kept in the range described above. The reaction may be terminated before the content of the formed optically active α-substituted organic acid represented by formula (II) is not lowered. The reaction is generally carried out until reactivity reaches 8 to 60%.

The desired product of the present invention can be recovered in the following manner.

After insoluble matter, such as bacteria are removed from the cultured solution, the pH of the resulting solution is adjusted to 8.5. The unreacted compound of formula (I) is extracted with a solvent such as n-butanol, benzene, diethyl ether or chloroform, to remove it. The pH of the resulting solution is then adjusted to 2 and extraction is carried out with a solvent such as n-butanol, benzene, diethyl ether or chloroform, whereby the desired product can be recovered. The product can be purified by means of silica gel column chromatography, followed by elution with a solvent, such as a mixture of, e.g., hexane, diethyl ether, chloroform and methanol.

It is believed that the reaction mechanism of the present invention is such that the enzyme which converts the nitrile or amide into a carboxylic acid, that is, amidase, nitrilehydratase or nitrilase, reacts selectively with only one isomer of the racemic nitrile or amide. Namely, it is believed that the enzyme reaction rate varies greatly with the optical isomer. Accordingly, when an optically active organic acid is prepared by the process of the present invention, an optically active nitrile or amide is consequently left or formed as an unreacted material or an intermediate. The nitrile or amide can be easily converted into an optically active organic acid by hydrolyzing it in the presence of an acid. Namely, any R isomer and S isomer or (+) isomer and (−) isomer of an organic acid can be prepared in the present invention. When either one isomer of an optically active organic acid is to be prepared, an optically active nitrile or amide which is an unreacted material or an intermediate is racemized, e.g., by a reaction using an alkali, such as ammonia, and the resulting racemic nitrile or amide can be used as the starting material of the present invention. Accordingly, the desired optically active organic acids can be prepared in high yields on an industrial scale.

Amidase, nitrile hydratase or nitrilase isolated from the microorganisms of the present invention have such specificity that there is a possibility that the reaction rate will vary greatly with the optical isomer when reacted with the racemic nitrile or amide. The present inventors isolated nitrilase or amidase having such specificity from the above-described microorganisms. Nitrilase isolated from Acinetobacter sp. AK 226 strain will be illustrated below by way of example.

(1) Preparation of the enzyme

To prepare nitrilase of the present invention, Acinetobacter sp. AK 226 strain is cultured in the above-described medium. The material for accelerating reaction activity is added and the strain is cultured for 1 to 3 days under the above-described culture conditions.

Nitrilase is recovered from the resulting culture medium and can be purified by conventional enzyme purifying methods. Bacteria is collected by centrifugation and disintegrated by an ultrasonic treatment or a mechanical means such as daino mill. Solids, such as cell memblens, are removed by centrifugation. The resulting crude enzyme is subjected to fractional ultra-centrifugation, saltingout treatment, precipitation treatment with organic solvents and further purification by means of adsorption chromatography, ion-exchange chromatography, and/or gel permeation chromatography. This is described in more detail in the example.

(2) Assay (measurement of titer)

0.5 μmol of potassium phosphate buffer solution (pH 8.0) and 1.34 μmol of 2-(4'-isobutylphenyl)propionitrile are added to an appropriate amount of an enzyme solution so as to give a volume of 0.5 ml. After the mixture is reacted at 30° C. for 30 minutes, 0.1 ml of 80% acetic acid is added thereto to stop the reaction. The amounts of 2-(4'-isobutylphenyl)propionic acid and ammonia are measured. The amount of 2-(4'-isobutylphenyl)propionic acid is measured by means of high performance liquid chromatography wherein a Bondapack C18 column is used and a solvent obtained by mixing 0.05M phosphate buffer solution (pH 3) with 50% (v/v) of acetonitrile is used. The assay is performed at an absorbance of 254 nm. The amount of ammonia formed is measured according to *J. Clin. Path.*, 13, 156 (1960).

The amount of enzyme required for forming 1 μmol of 2-(4'-isobutylphenyl)propionic acid or ammonia per one minute is referred to as one unit.

(3) Properties of the enzyme

Nitrilase of the present invention is isolated in a pure form and has the following properties.

(i) Function: One molecule of a nitrile compound is hydrolyzed to form one molecule of an organic acid and one molecule of ammonia.

The reaction rate with the S isomer of racemic 2-(4'-isobutylphenyl)propionitrile is much higher than that of the R isomer thereof. Accordingly, optically active S-(+)-2-(4'-isobutyl)propionic acid is formed. This is described in the example.

(ii) Substrate specificity

The enzyme reacts with many nitrile compounds such as aliphatic nitriles and aromatic nitriles given in the following Table 2. However, it does not react with compounds having an amino group at the α-position.

TABLE 2

| Substrate | Relative activity ($\times 10^2$%) |
|---|---|
| Acetonitrile | 45.3 |
| n-Butyronitrile | 17.4 |
| n-Capronitrile | 5.93 |
| iso-Capronitrile | 8.12 |
| Acrylonitrile | 144 |
| Methacrylonitrile | 68.4 |
| Hydroxyacetonitrile | 11.4 |
| Chloroacetonitrile | 108 |
| 2,3-Dibromopropionitrile | 90.3 |
| Benzyl cyanide | 26.2 |
| α-Phenylpropionitrile | 0.534 |
| 2-(4'-Isobutylphenyl)propionitrile | 1.00 |
| 2-Phenylglycinonitrile | 0.000 |
| Thiopheneacetonitrile | 45.5 |
| Nicotinonitrile | 52.7 |
| Benzonitrile | 94.1 |
| o-Tolunitrile | 0.743 |
| m-Tolunitrile | 74.8 |
| p-Tolunitrile | 6.57 |
| m-Nitrobenzonitrile | 47.6 |
| o-Fluorobenzonitrile | 50.4 |
| m-Fluorobenzonitrile | 66.8 |
| p-Fluorobenzonitrile | 83.9 |
| m-Chlorobenzonitrile | 68.9 |
| Glutaronitrile | 50.9 |
| m-Phthalonitrile | 80.7 |

(iii) Optimum pH: about pH 8.0

(iv) pH stability: Stable at a pH 5.8 to 6.7 when treated with a buffer solution having various pH at 60° C. for 60 minutes.

(v) Optimum temperature: Maximum effect is obtained at a temperature of about 45° to 60° C.

(vi) Absorption spectrum: Maximum absorption spectrum at about 223 nm and 280 nm.

(vii) Molecular weight: About 580,000 measured by means of high performance liquid chromatography with Asahipak GS-620(a product of Asahi Chemical Industry Co., Ltd.)

(viii) Molecular weight of subunit: 42,000 to 47,000 calculated by electrophoresis of SDS-polyacrylamide gel.

As stated above, the above enzyme is a novel nitrilase which reacts with a wide range of aliphatic nitriles and aromatic nitriles. Further, the above enzyme has such an excellent effect that 2-(4'-isobutylphenyl)-propionitrile is hydrolyzed with optical specificity when said nitrile is used as substrate.

The present invention is now illustrated in greater detail by reference to the following examples which, however, are not to be construed as limiting the present invention in any way. In the following examples, % is by weight unless otherwise stated.

EXAMPLE 1

Preparation of S-(+)-α-phenylpropionic acid

To 2,000 ml of a sterilized culture medium containing 1% glucose, 0.5% yeast extract, 0.5% peptone, 0.12% monopotassium phosphate, 0.08% dipotassium phosphate, 0.02% magnesium sulfate, 0.003% ferrous sulfate, 0.1% sodium chloride and 0.1% isobutyronitrile and having a pH of 7.2, 2% of *Corynebactetrium nitrilophilus* ATCC 21419 strain which was previously cultured on the same medium was inoculated. The media was cultured at 32° C. for two days by means of shaking culture. After culture, bacteria (5.2 g; dry weight) were collected by centrifugation, suspended in 160 ml of 0.01M phosphate buffer (pH 8.0) and placed in an Erlenmeyer flask. 1.6 g of α-phenylpropionitrile was added thereto and the reaction of the mixture took place while shaking it at 32° C. After 20 hours, the reaction was terminated and the bacteria were removed by centrifugal separation. The pH of the resulting supernatant liquid was adjusted to 8.5. 200 ml of chloroform was added thereto to extract and remove the unreacted α-phenylpropionitrile. The pH of water layer was adjusted to from 1.0 to 2.0 with hydrochloric acid. 200 ml of chloroform was added thereto to extract the desired product. The extract was concentrated under reduced pressure and purified by means of a silica gel column (500 mg, adjusted with hexane), eluting with hexane-diethyl ether (95:5 by volume). The desired eluate was concentrated under reduced pressure to afford 475 mg of S-(+)-α-phenylpropionic acid.

Specific rotary power: $[\alpha]_D^{25} = +75°$ (C=1.65 chloroform)

Optical purity was 98% from specific rotary power. TLC chromatography and high performance liquid chromatography revealed that the product was single.

EXAMPLE 2

Preparation of S-(+)-α-phenylpropionic acid:

In the same way as in Example 1, to 500 ml of the sterilized culture medium 2% of the microorgnism which was previously cultured on the same medium was inoculated. The media was cultured at 32° C. for two days by means of shaking culture. After culture, the bacteria was collected by centrifugal separation, suspended in 30 ml of 0.01M phosphate buffer (pH 8.0) and placed in an Erlenmeyer flask. 300 mg of α-phenylpropionitrile was added thereto and the mixture was reacted at 32° C. with shaking.

After removal of the bacteria from the reaction solution by centrifugal separation, extraction with chloroform was carried out in the same way as in Example 1 to obtain α-phenylpropionic acid. The optical specificity thereof was examined by means of high performance liquid chromatography. The results are shown in Table 3 below.

TABLE 3

| Microorganism | Reaction time (hr) | Amount of product (mg) | Ratio of S-(+)-α-phenylpropionic acid/R-(−)-α-phenyl-propionic acid |
|---|---|---|---|
| *Pseudomonas fluorescens* NRRL B981 | 10 | 69 | 98/2 |
| *Rhodopseudomonas sphaeroides* ATCC 11167 | 12 | 81 | 90/10 |
| *Rhodococcus sp.* AK 32 | 24 | 94 | 95/5 |
| *Bacillus subtilis* CN5 | 8 | 98 | 98/2 |
| *Mycobacterium sp.* AC777 | 12 | 85 | S-isomer only |
| *Corynebacterium sp.* KO-2-4 | 10 | 110 | 97/3 |

The optical specificity was determined using high performance liquid chromatography according to the method for analyzing S-(−)-1-(naphtyl)ethylamide [*Journal of Chromatography*, 378, p409~418 (1986)].

EXAMPLE 3

Preparation of S-(+)-α-phenylpropionic acid

Bacteria were cultured, collected by centrifugal separation, suspended in 30 ml of 0.01M phosphate buffer solution (pH 8.0) and placed in an Erlenmeyer flask, as in Example 2. 300 mg of α-phenylpropioniamide was added thereto and the reaction was carried out at 32° C. with shaking.

After the bacteria was removed from the reaction solution by centrifugal separation, α-phenylpropionic acid was obtained in the same way as in Example 2. Optical specificity was examined by high performance liquid chromatography. The results are shown in Table 4 below.

TABLE 4

| Microorganism | Reaction time (hr) | Amount of product (mg) | Ratio of S-(+)-α-phenylpropionic acid/R-(−)-α-phenylpropionic acid |
|---|---|---|---|
| *Pseudomonas fluorescens* IFO 3081 | 10 | 90 | S-isomer only |
| *Rhodopseudomonas sphaeroides* ATCC 11167 | 10 | 62 | " |
| *Corynebacterium nitrilophilus* ATCC 21419 | 6 | 97 | 98/2 |
| *Rhodococcus sp.* AK 32 | 18 | 72 | 93/7 |
| *Bacillus subtilis* CN5 | 10 | 80 | S-isomer only |
| *Mycobacterium sp.* AC777 | 6 | 106 | 99/1 |
| *Pseudomonas fluorescens* NRRL B981 | 6 | 85 | 99/1 |

EXAMPLE 4

Preparation of S-(+)-Ibuprofen

In the same way as in Example 1, to 500 ml of the sterilized culture medium 2% of Acinetobacter sp. AK 226 strain which was previously cultured on the same medium was inoculated. The media was cultured at 32° C. for 35 hours. After culture, the bacteria was collected by centrifugal separation, suspended in 30 ml of 0.1M phosphate buffer (pH 8.0) and placed in an Erlenmeyer flask. 90 mg of 2-(4'-isobutylphenyl)propionitrile was added thereto and the reaction was carried out at 32° C. with shaking. After 16 hours, the reaction was terminated and bacteria were removed by centrifugal separation. The pH of the resulting supernatant liquid was adjusted to 8.5. 30 ml of chloroform was added thereto to extract and remove the unreacted 2-(4'-isobutylphenyl)propionitrile. After the pH of the water layer was adjusted to from 1.0 to 2.0 with hydrochloric acid, 30 ml of chloroform was added thereto to extract the desired product. The extract was concentrated under reduced pressure and purified by means of silica gel column chloromatography, eluting with hexane-diethyl ether (3:1 by volume). The desired eluate was concentrated under reduced pressure to give 52 mg of S-(+)-2-(4'-isobutylphenyl)propionic acid.

$[\alpha]_D^{20} = +52.7°$ (C=1, ethanol)

Melting point: 49° C.

Optical purity was 95% from specific rotary power.

TLC chromatography and high performance liquid chromatography revealed that the product was single.

EXAMPLE 5

Preparation of S-(+)-Naproxen

In the same way as in Example 1, to 500 ml of the sterilized culture medium 2% of Rhodococcus sp. AK 32 strain which was previously cultured on the same medium was inoculated. The media was cultured at 32° C. for 30 hours. After culture, bacteria were collected by centrifugal separation, suspended in 30 ml of 0.1M phosphate buffer (pH 8.0) and placed in an Erlenmeyer flask. 90 mg of 2-(6'-methoxy-2'-naphtyl)propionitrile was added thereto and the reaction was carried out at 32° C. with shaking. After 30 hours, the reaction was terminated and bacteria were removed by centrifugal separation. The pH of the resulting supernatant liquid was adjusted to 8.5. 30 ml of chloroform was added thereto to extract and remove the unreacted material and by-products. The pH of the aqueous layer was adjusted to from 1.0 to 2.0 with hydrochloric acid, 30 ml of chloroform was added thereto to extract the desired product. The extract was concentrated under reduced pressure and purified by means of silica gel column chromatography, eluting with hexanediethyl ether (7:3 by volume). The desired eluate was concentrated under reduced pressure to give 37 mg of S-(+)-2-(6'-methoxy-2'-naphtyl)propionic acid.

$[\alpha]_D^{20} = +62.8°$ (C=1, chloroform)

Melting point: 153° C.

Optical purity was 95% from specific rotary power.

TLC chromatography and high performance liquid chromatography revealed that the product was single.

EXAMPLE 6

Preparation of (+)-Pranoprofen

In the same way as in Example 1, to 500 ml of the sterilized culture medium 5% of Corynebacterium sp. KO-2-4 which was previously cultured on the same medium was inoculated. Culturing was conducted at 32° C. for 35 hours. After culturing, bacteria were collected by centrifugal separation, suspended in 30 ml of 0.1M phosphate buffer (pH 8.0) and placed in an Erlenmeyer flask. 90 mg of 2-(5H-[1]benzopyrano[2,3-b]pyridine-7-yl)propionitrile was added thereto and the reaction was carried out at 32° C. while vigorously shaking the mixture. After 24 hours, the reaction was terminated and bacteria were removed by centrifugal separation. The pH of the resulting supernatant liquid was adjusted to 8.5. 30 ml of chloroform was added thereto to extract and remove the raw nitrile compound and the corresponding amide compound. The pH of the aqueous layer was adjusted to from 1.0 to 2.0 with hydrochloric acid and 30 ml of chloroform was added thereto to extract the desired product. The extract was concentrated under reduced pressure and purified by means of silica gel column chromatography, eluting with hexane-diethyl ether (3:1 by volume). The desired eluate was concentrated under reduced pressure to give 42 mg of (+)-2-(5H-[1]benzopyrano[2,3-b]pyridine-7-yl)propionic acid [(+)-Pranoprofen].

$[\alpha]_D^{20} = +43.3°$ (C=1.0, methanol)

Melting point: 184°–185° C.

Optical purity was 96% from specific rotary power.

TLC chromatography and high performance liquid chromatography revealed that the product was single.

EXAMPLE 7

Purification of nitrilase of Acinetobacter sp. AK 226

The culture procedure of Example 4 was repeated except that 2 l of culture medium containing 1% ammonium acetate in place of glucose was used. 40 g of bacteria was collected by centrifugal separation, washed with 0.01M potassium phosphate buffer solution (pH 6.5) and then suspended in 160 ml of 0.03M potassium phosphate buffer solution (pH 6.5). The suspension was subjected to an ultrasonic treatment (9 KHz) for 30 minutes to disrupt cells. The disrupted cells were removed by centrifugal separation (15,000×g for 20 minute] to obtain a cell-free extract. The extract was dialyzed against a 0.03 M potassium phosphate buffer solution (pH 6.5) and subjected to centrifugal separation (100,000×g for 2 hours). The supernatant liquid was passed through a DEAE-cellulose column to elute enzyme with a linear gradient of 0.05M potassium phosphate buffer solution (pH 6.5) containing 0 to 0.5M sodium chloride. Active fractions were collected, dialyzed against 0.01M potassium phosphate buffer solution (pH 6.5) and passed through a hydroxyapatite column to elute enzyme with a linear gradient of 0.01 to 0.2M potassium phosphate buffer solution (pH 6.5). Active fractions were collected, dialyzed against 0.03M potassium phosphate buffer solution (pH 6.5) and purified by means of the DEAE-cellulose column and the hydroxyapatite in a similar manner to that described above. Active fractions were concentrated by means of ultrafiltration and subjected to gel permeation chromatography using Sephacryl S-400 equilibrated by using a 0.05M potassium phosphate buffer solution (pH 6.5)]. In this way, nitrilase was uniformly purified. The progress of the purification is shown in Table 5 below.

TABLE 5

| Stage | Total activity (unit) | Total protein (mg) | Specific activity (unit/mg) |
| --- | --- | --- | --- |
| 1. Cell-free extract | 156 | 4400 | 0.0354 |
| 2. Ultra-centrifugal separation | 131 | 3460 | 0.0380 |
| 3. First DEAE-cellulose | 69.8 | 1270 | 0.0549 |
| 4. First hydroxyapatite | 65.6 | 943 | 0.0696 |
| 5. Second DEAE-cellulose | 45.6 | 541 | 0.0843 |
| 6. Second hydroxyapatite | 33.7 | 329 | 0.102 |
| 7. Sephacryl S-400 | 31.4 | 201 | 0.156 |

EXAMPLE 8

The progress of the formation of S-(+)-Ibuprofen

Nitrilase uniformly purified in Example 7 was used and the progress of the reaction was examined under the following conditions.

One ml of the reaction solution containing 100 μmol of potassium phosphate buffer solution (pH 8.0), 4.77 μmol of 2-(4'-isobutylphenyl)propionitrile and 0.02 unit of nitrilase was thoroughly shaken at 32° C. to carry out the reaction. The amounts of 2-(4'-isobutylphenyl)-propionitrile, 2-(4'-isobutylphenyl)propionic acid and ammonia for each reaction time were determined. The results are shown in the Figure. The optical purity of the formed S-(+)-2-(4'-isobutylphenyl)propionic acid was 98% for 6 hours, 96% for 24 hours and 95% for 40 hours.

EXAMPLE 9

Preparation of R-(−)-Ibuprofen

The unreacted 2-(4'-isobutylphenyl)propionitrile extracted with chloroform in Example 4 was concentrated under reduced pressure. To this sample were added 5 ml of deionized water and 5 ml of concentrated sulfuric acid. The mixture was reacted at 105° C. with stirring for 7 hours. After the completion of the reaction, 20 ml of chloroform was added thereto to extract the desired product. The extract was concentrated under reduced pressure and purified by means of silica gel column chromatography, eluting with hexane-diethyl ether (3:1 by volume). The desired eluate was concentrated under reduced pressure to afford 44 mg of R-(−)-2-(4'-isobutylphenyl)propionic acid.

$[\alpha]_D^{20} = -50.0°$ (C=1, ethanol)

Melting point: 48°–49° C.

The product had an R isomer content of 95% from specific rotary power.

Thin layer chromatography revealed that the product exhibited a single spot.

EXAMPLE 10

Preparation of S-(+)-Ibuprofen

Acinetobacter sp. AK 226 strain was cultured in the same way as in Example 4. Bacteria (950 mg; dry weight) were collected by centrifugal separation, suspended in 30 ml of 0.1M phosphate buffer (pH 8.0) and placed in an Erlenmeyer flask. 5 ml of hexane containing 1.5 g of 2-(4'-isobutylphenyl)propionitrile was added to the suspension and the reaction was carried out at 32° C. with shaking. After 16 hours, the reaction was terminated and bacteria were removed by centrifugal separation. The pH of the aqueous layer was adjusted to 8.5 by adding 270 ml of water and sodium hydroxide. The hexane layer was removed. Further, 300 ml of chloroform was added to completely remove the unreacted 2-(4'-isobutylphenyl)-propionitrile. The pH of the aqueous layer was adjusted to 1.0 with hydrochloric acid. 300 ml of chloroform was added thereto to extract the desired product. The extract was concentrated under reduced pressure and purified by means of silica gel column chromatography, eluting with hexane-diethyl ether (3:1 by volume). The desired eluate was concentrated under reduced pressure to give 670 mg of S-(+)-2-(4'-isobutylphenyl)propionic acid.

$[\alpha]_D^{20} = +56.0°$ (C=1, ethanol)

Melting point: 49°–50° C.

The product had an S isomer content of 98.5% from specific rotary power.

Thin layer chromatography revealed that the product exhibited a single spot.

EXAMPLE 11

Preparation of R-(−)-mandelic acid

To 100 ml of a sterilized culture medium containing 1% glucose, 0.5% yeast extract, 0.5% peptone, 0.2% dipotassium phosphate, 0.1% sodium chloride and 0.003% ferrous sulfate and having a pH of 7.0, 4% of Alcaligenes faecalis ATCC 8750 strain which was previously cultured on the same medium was inoculated. The media was cultured at 32° C. for two days by shaking culture. After culturing the bacteria (60 mg; dry weight) was collected by centrifugal separation and suspended in 150 ml of 0.1M phosphate buffer (pH 8.0). 250 mg of mandelonitrile was added to 50 ml of the suspension and the mixture was reacted at 32° C. with shaking for 4 hours. The bacteria were removed from the reaction solution by centrifugal separation. The pH of the resulting supernatant liquid was adjusted to 8.5. 50 ml of chloroform was added thereto to extract the unreacted mandelonitrile. The pH of the aqueous layer was adjusted to 1.0 with hydrochloric acid. 40 ml of diethyl ether was added thereto to extract the desired product. The extract was concentrated under reduced pressure and purified by means of column chromatography on silica gel (500 mg, adjusted with hexane), eluting with hexane-ethyl acetate (50:50 by volume). The desired eluate was concentrated under reduced pressure to afford 76 mg of R-(−)-mandelic acid.

$[\alpha]_D^{25} = -141°$ (C=1, H$_2$O)

Melting point: 130°-132° C.

The R isomer content was 92.2% from specific rotary power.

Analysis by high performance liquid chromatography was made according to *Journal of Chromatography*, 216, 06(1981). It was found that the sample had a R isomer content of 91%.

EXAMPLE 12

Preparation of R-(−)-mandelic acid:

One liter of the culture medium having the same composition as that of Example 11 was used. To the medium, each of *Pseudomonas vesicularis* ATCC 11426 strain and *Candida tropicalis* ATCC 20311 was inoculated. Culture was conducted. The collected cells (1.76 g and 7.14 g; dry weight) were suspended in 100 ml and 500 ml of 1.0M phosphate buffer (pH 8.0), respectively. 2.0 g of mandelamide was added to 100 ml of each suspension. The mixtures were reacted at 32° C. for 40 hours under shaking. Insoluble matter such as cells were removed from each reaction soution by centrifugal separation. The pH of the supernatant liquids were adjusted to 1.0 with hydrochloric acid. 50 ml of diethyl ether was added thereto to extract the desired product. The extracts were purified in the same way as in Example 11.

There was obtained 795 mg of R-(−)-mandelic acid from the reaction solution of *Pseudomonas vesicularis* ATCC 11426.

$[\alpha]_D^{25} = -153°$ (C=1, H$_2$O)

Melting point: 134°-135° C.

There was obtained 940 mg of R-(−)-mandelic acid from the reaction mixture of *Candida tropicalis* ATCC 20311.

$[\alpha]_D^{25} = -147°$ (C=0.5, H$_2$O)

Melting point: 133°-134° C.

The R isomer contents of the purified samples calculated from specific rotary power were 100% and 98%, respectively.

EXAMPLE 13

Preparation of S-(−)- 2-chloropropionic acid

In the same way as in Example 11, Mycobacterium sp. AC777 was cultured. The bacteria (710 mg; dry weight) was suspended in 80 ml of 0.1 M phosphate buffer (pH 8.0). 200 mg of 2-chloropropionitrile was added to 20 ml of the suspension. The mixture was reacted at 32° C for two hours under shaking. Insoluble matter was removed from the reaction solution by centrifugal separation. The pH of the supernatant liquid was adjusted with sodium hydroxide to 9. 20 ml of chloroform was added to the supernatant liquid to remove the unreacted 2-chloropropionitrile. The pH of the aqueous layer was adjusted to 1 with hydrochloric acid. 20 ml of n-butanol was added to said aqueous layer to extract the desired product. The n-butanol layer was concentrated under reduced pressure and purified by means of column chromatography on silica gel (500 mg, adjusted with chloroform), eluting with chloroform-methanol (10:1 by volume). The desired eluate was concentrated under reduced pressure to give 59 mg of S-(−)-2-chloropropionic acid.

$[\alpha]_D^{25} = -8.4°$ (C=1, H$_2$O)

The S isomer content calculated from specific rotary power was 80%.

High performance liquid chromatography and TLC chromatography revealed that the product was single.

EXAMPLE 14

Preparation of S-(−)-2-bromopropionic acid:

In the same way as in Example 12, Mycobacterium sp. AC777 strain was cultured. The bacteria (710 mg; dry weight) was suspended in 20 ml of 0.1 M phosphate buffer (pH 8.0). 200 mg of 2-bromopropionitrile was added to the suspension. The mixture was reacted at 32° C for 30 hours under shaking. Insoluble matter was removed from the reaction solution by centrifugal separation. The pH of the supernatant liquid was adjusted with sodium hydroxide to 8.5. 20 ml of chloroform was added thereto to extract the unreacted 2-bromopropionitrile. The pH of the aqueous layer was adjusted to 1.5 with sulfuric acid. 40 ml of n-butanol was added thereto to extract the desired product. The n-butanol layer was concentrated under reduced pressure and purified by means of column chromatography on silica gel (500 mg, adjusted with chloroform), eluting with chloroform-methanol (10:1 by volume). The desired eluate was concentrated under reduced pressure to give 45 mg of S-(−)-2-bromopropionic acid.

$[\alpha]_D^{27} = -19.9°$ (C=1, methanol)

The S isomer content of the product was 86% from specific rotary power.

High performance liquid chromatography and TLC chromatography revealed that the product was single.

EXAMPLE 15

Preparation of (+)-2-phenoxypropionic acid

In the same way as in Example 11, Mycobacterium sp. AC777 strain was cultured. The bacteria (710 mg; dry weight) was suspended in 100 ml of 0.1 M phosphate buffer (pH 8.0). 100 mg of 2-phenoxypropionitrile was added to 10 ml of the suspension. The mixture was reacted at 32° C for 3 hours under shaking. Insoluble matter was removed from the reaction solution by centrifugal separation. The pH of the supernatant liquid was adjusted with sodium hydroxide to 9. 10 ml of chloroform was added thereto to remove the unreacted 2-phenoxypropionitrile and 2-phenoxypropionamide. The pH of the water layer was adjusted to 1 with hydrochloric acid. 10 ml of chloroform was added to the water layer to extract the desired product. The chloroform layer was concentrated under reduced pressure and purified in the same way as in Example 1 to give 34 mg of 2-phenoxypropionic acid. In the same way as in Example 2, optical specificity was examined by high performance liquid chromatography. It was found that only (+) isomer was formed.

EXAMPLE 16

Preparation of (+)-2-phenoxypropionic acid

In the same way as in Example 11, Rhodococcus sp. AK 32 strain was cultured. Bacteria (270 mg; dry weight) was suspended in 100 ml of 0.1 M phosphate buffer (pH 8.0). 100 mg of 2-phenoxypropionamide was added to 10 ml of the suspension. The mixture was reacted at 32° C under shaking for 3 hours. Insoluble matters were removed from the reaction solution by centrifugal separation. The pH of the supernatant liquid was adjusted with sodium hydroxide to 9. 10 ml of chloroform was added thereto to remove the unreacted amide.

The pH of the supernatant liquid was adjusted to 1 with hydrochloric acid. 10 ml of chloroform was added thereto to extract the desired product. The chloroform layer was concentrated under reduced pressure and purified in the same way as in Example 1 to give 42 mg of 2phenoxypropionic acid. In the same way as in Example 2, the optical specificity of this sample was examined by high performance liquid chromatography. It was found that only (+) isomer was formed.

EXAMPLE 17

Preparation of S-(+)-2-phenyl-n-butyric acid 150 mg of 2-phenyl-n-butyronitrile was added to 10 m of a suspension of bacteria of Rhodococcus sp. AK 32 strain cultured in the same way as in Example 5. The mixture was reacted at 32° C under shaking for 18 hours. Insoluble matters were removed from the reaction mixture by centrifugal separation. The pH of the supernatant liquid was adjusted with sodium hydroxide to 8.5. 30 ml of chloroform was added thereto to remove the unreacted nitrile and the corresponding amide. The pH of the aqueous layer was adjusted to 2.0 with hydrochloric acid. 30 ml of chloroform was added thereto to extract the desired product. The extract was concentrated under reduced pressure and purified in the same way as in Example 1 to give 64 mg of S-(+)-2-phenyl-n-butyric acid.

$[\alpha]_D^{19} = +80.0°$ (C=0.9, toluene)

Optical purity was 93% from specific rotary power.

TLC chromatography and high performance liquid chromatography revealed that the product was single.

EXAMPLE 18

Preparation of S-(−)-3-chloro-2-methylpropionic acid

In the same way as in Example 11, Mycobacterium sp. AC777 was cultured. 710 mg (dry weight) of bacteria was suspended in 100 ml of 0.1 M phosphate buffer (pH 8.0) and placed in Erlenmeyer flask. 500 mg of 3-chloro-2-methylpropionitrile was added to 50 ml of the suspension. The mixture was reacted at 32° C with shaking for 4 hours. Bacteria were removed from the reaction mixture by centrifugal separation. The pH of the supernatant liquid was adjusted to 1.0 with hydrochloric acid. 30 ml of n-butanol was added thereto to extract the desired product. The extract was concentrated under reduced pressure and purified by means of column chromatography on silica gel (1 g, adjusted with chloroform), eluting with chloroformmethanol (10:1 by volume). The desired eluate was concentrated under reduced pressure to give 243 mg of S-(−)-3-chloro-2-methylpropionic acid.

$[\alpha]_D^{25} = -14.0°$ (C=1, MeOH)

This sample was reacted with (1R, 2R)-(−)-1-(4-nitrophenyl)-2-amino-1,3-propanediol to amidate it. The amide was analyzed by high performance liquid chromatography [*Chromatoqraphia* 24, 477 (1987)]. A single peak was found and only S isomer was formed.

When the present invention is utilized, various optically active u-substituted organic acids can be prepared from optically inactive starting materials under normal atmospheric and room temperature reaction conditions by using the present microorganisms. Accordingly, the present invention is very economically advantageous.

Further, optically active α-substituted organic acids having an optical purity of as high as at least 80%, or as extremely high as at least 90% according to the types of organic acids, can be obtained in high yields by the present invention.

While the invention has been described in detail and with reference to specific embodiments thereof, it will be apparent to one skilled in the art that various changes and modifications can be made therein without departing from the spirit and scope thereof.

What is claimed is:

1. A process for producing optically active α-substituted organic acid represented by formula (II), comprising the steps of:

(a) treating a racemic α-substituted nitrile represented by formula (I) with a microorganism which possesses an enantioselective nitrilase or mixture of a nitrile hydratase and an enantioselective amidase capable of converting said racemic α-substituted nitrile into its respective optically active organic acid, wherein said microorganism is selected from the group consisting of the microorganism of the genera Alcaligenes, Pseudomonas, Rhodopseudomonas, Corynebacterium, Acinetobacter, Bacillus, Mycobacterium and Rhodococcus, or preparations thereof; and (b) recovering the resulting optically active α-substituted organic acid represented by formula (II):

wherein $R_1$ and $R_2$ each represent a halogen atom, a hydroxyl group, a substituted or unsubstituted alkyl group, a substituted or unsubstituted cycloalkyl group, a substituted or unsubstituted alkoxy group, a substituted or unsubstituted aryl group, a substituted or unsubstituted aryloxy group or a substituted or unsubstituted heterocyclic group, wherein a substituent group is selected from the group consisting of a halogen atom, a hydroxyl group, a thiol group, a nitro group, an amino group, an aryl group, an aryloxy group, a heterocyclic group having from 3 to 15 carbon atoms and containing one or more hetero-atoms including a nitrogen atom, an oxygen atom or a sulfur atom, an alkyl group having from 1 to 8 carbon atoms, an alkoxy group having from 1 to 8 carbon atoms and an acyl group having from 1 to 10 carbon atoms, with the proviso that $R_1$ and $R_2$ are different from each other; and X represents a nitrile group,

wherein $R_1$ and $R_2$ are as defined for formula (I).

2. The process according to claim 1, wherein said alkyl group has from 1 to 8 carbon atoms, said alkoxy group has from 1 to 8 carbon atoms, said cycloalkyl group has from 3 to 8 carbon atoms, said aryl group is phenyl or naphthyl, said aryloxy group is phenyloxy or naphthloxy, and said heterocyclic group has one or more hetero-atoms selected from the group consisting of nitrogen, oxygen and sulfur, and has from 3 to 15 carbon atoms.

* * * * *